US011810676B2

(12) United States Patent
Brock et al.

(10) Patent No.: US 11,810,676 B2
(45) Date of Patent: Nov. 7, 2023

(54) VERIFIED PERMISSIONED BLOCKCHAINS

(71) Applicant: International Business Machines Corporation, Armonk, NY (US)

(72) Inventors: Bishop C. Brock, Coupland, TX (US); Frank Liu, Austin, TX (US); Thomas S. Hubregtsen, Hassfurt (DE)

(73) Assignee: International Business Machines Corporation, Armonk, NY (US)

( * ) Notice: Subject to any disclaimer, the term of this patent is extended or adjusted under 35 U.S.C. 154(b) by 86 days.

(21) Appl. No.: 16/199,570

(22) Filed: Nov. 26, 2018

(65) Prior Publication Data

US 2020/0167338 A1    May 28, 2020

(51) Int. Cl.

| | |
|---|---|
| *G06F 7/00* | (2006.01) |
| *G16H 50/70* | (2018.01) |
| *G06F 16/23* | (2019.01) |
| *H04L 9/06* | (2006.01) |
| *G06F 16/27* | (2019.01) |
| *G06N 20/00* | (2019.01) |
| *G06N 5/04* | (2023.01) |
| *G06V 10/774* | (2022.01) |
| *G06V 10/94* | (2022.01) |
| *G16H 30/00* | (2018.01) |
| *H04L 9/00* | (2022.01) |

(52) U.S. Cl.
CPC ......... *G16H 50/70* (2018.01); *G06F 16/2379* (2019.01); *G06F 16/27* (2019.01); *G06N 5/04* (2013.01); *G06N 20/00* (2019.01); *G06V 10/774* (2022.01); *G06V 10/95* (2022.01); *H04L 9/0637* (2013.01); *G06V 2201/03* (2022.01); *G16H 30/00* (2018.01); *H04L 9/50* (2022.05)

(58) Field of Classification Search
CPC ... H04L 9/3247; H04L 9/3236; H04L 63/126; H04L 9/0637; H04L 9/50; G06F 16/27; G06F 16/2379; G06N 20/00; G06N 5/04; G06K 9/66; G16H 50/70; G16H 30/00; G06V 10/95; G06V 10/774; G06V 2201/03
USPC .......................................... 707/703, 769, 786
See application file for complete search history.

(56) References Cited

U.S. PATENT DOCUMENTS

| | | | |
|---|---|---|---|
| 9,667,427 B2 | 5/2017 | Oberhauser et al. | |
| 9,749,140 B2 | 8/2017 | Oberhauser et al. | |
| 10,365,922 B1 * | 7/2019 | Wang ...................... | G06F 21/10 |

(Continued)

FOREIGN PATENT DOCUMENTS

CN            106453377 A         2/2017

OTHER PUBLICATIONS

Anonymously; "Intelligent Machine Learning Algorithm to Protect Privacy"; http://ip.com/IPCOM/000250567D; Aug. 3, 2017.

(Continued)

*Primary Examiner* — Md I Uddin (57) ABSTRACT

An example operation may include one or more of receiving an example in a blockchain network, distributing the example to a plurality of endorsing peers of the blockchain network, performing, by one or more of the endorsing peers, automated analysis of the example to determine an inference for the example, determining if there is a consensus of inference amongst the plurality of endorsing peers, and committing the example to a blockchain of the blockchain network when there is a consensus of inference.

17 Claims, 9 Drawing Sheets

(56) References Cited

U.S. PATENT DOCUMENTS

2017/0109657 A1     4/2017    Marcu et al.
2019/0205773 A1*   7/2019    Ackerman .......... G06F 21/6227

OTHER PUBLICATIONS

Anonymously; "System and Method of Secure and Permissioned Sharing of Cognitive Patterns in a Marketplace"; http://ip.com/IPCOM/000250922D; Sep. 14, 2017.

Husain, F.; "Synechron's Blockchain Accelerator Program"; Synetimes, Edition 3, www.synechron.com. 2017.

IBM; "Using quantized probabilities to overcome the requirement of fully observed data in generic Bayesian networks structure learning algorithms"; http://ip.com/IPCOM/000183826D; Jun. 2, 2009.

Outlier Ventures Research; "Blockchain-Enabled Convergence—Understanding The Web 3.0 Economy"; Outlier Ventures Capital LLP.; 2016.

* cited by examiner

VERIFIED PERMISSIONED BLOCKCHAINS

TECHNICAL FIELD

This application generally relates to secure blockchains, and more particularly, to verified permissioned blockchains.

BACKGROUND

A ledger is commonly defined as an account book of entry, in which transactions are recorded. A distributed ledger is ledger that is replicated in whole or in part to multiple computers. A Cryptographic Distributed Ledger (CDL) can have at least some of these properties: irreversibility (once a transaction is recorded, it cannot be reversed), accessibility (any party can access the CDL in whole or in part), chronological and time-stamped (all parties know when a transaction was added to the ledger), consensus based (a transaction is added only if it is approved, typically unanimously, by parties on the network), verifiability (all transactions can be cryptographically verified). A blockchain is an example of a CDL. While the description and figures herein are described in terms of a blockchain, the instant application applies equally to any CDL.

A distributed ledger is a continuously growing list of records that typically apply cryptographic techniques such as storing cryptographic hashes relating to other blocks. A blockchain is one common instance of a distributed ledger and may be used as a public ledger to store information. Although, primarily used for financial transactions, a blockchain can store various information related to goods and services (i.e., products, packages, status, etc.). A decentralized scheme provides authority and trust to a decentralized network and enables its nodes to continuously and sequentially record their transactions on a public "block", creating a unique "chain" referred to as a blockchain. Cryptography, via hash codes, is used to secure an authentication of a transaction source and removes a central intermediary. A blockchain is a distributed database that maintains a continuously-growing list of records in the blockchain blocks, which are secured from tampering and revision due to their immutable properties. Each block contains a timestamp and a link to a previous block. A blockchain can be used to hold, track, transfer and verify information. Since a blockchain is a distributed system, before adding a transaction to the blockchain ledger, all peers need to reach a consensus status.

Supervised machine learning (ML) and deep learning (DL) requires numerous, validated training examples. A single organization may not be able to generate enough examples on its own. Therefore there is a need to share examples in a secure and controlled way.

In health/safety critical applications, the authenticity, correctness and security of training examples and subsequent inference is critical. For example, in medical diagnosis from images, doctors must sign-off on the veracity of training examples while preserving patient privacy.

What is required is an ability a system that can expand the source of training examples in a secure manner while providing consensus of inference.

SUMMARY

One example embodiment may provide a method that includes one or more of receiving an example in a blockchain network, distributing the example to a plurality of endorsing peers of the blockchain network, performing, by one or more of the endorsing peers, automated analysis of the example to determine an inference for the example, determining if there is a consensus of inference amongst the plurality of endorsing peers, and committing the example to a blockchain of the blockchain network when there is a consensus of inference.

Another example embodiment may provide a system that includes a blockchain network comprising a plurality of endorsing peers. The blockchain network may be configured to perform one or more of receive an example and distribute the example to a plurality of the endorsing peers, perform, by one or more of the endorsing peers, automated analysis of the example to determine an inference for the example, determine if there is a consensus of inference amongst the plurality of endorsing peers, and commit the example to a blockchain of the blockchain network when there is a consensus of inference.

A further example embodiment may provide a non-transitory computer readable medium comprising instructions, that when read by a processor, cause the processor to perform one or more of receiving an example in a blockchain network, distributing the example to a plurality of endorsing peers of the blockchain network, performing, by one or more of the endorsing peers, automated analysis of the example to determine an inference for the example, determining if there is a consensus of inference amongst the plurality of endorsing peers, and committing the example to a blockchain of the blockchain network when there is a consensus of inference.

DETAILED DESCRIPTION

It will be readily understood that the instant components, as generally described and illustrated in the figures herein, may be arranged and designed in a wide variety of different configurations. Thus, the following detailed description of the embodiments of at least one of a method, apparatus, non-transitory computer readable medium and system, as represented in the attached figures, is not intended to limit the scope of the application as claimed, but is merely representative of selected embodiments.

The instant features, structures, or characteristics as described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" may have been used in the description of embodiments, the application may be applied to many types of network data, such as, packet, frame, datagram, etc. The term "message" also includes packet, frame, datagram, and any equivalents thereof. Furthermore, while certain types of messages and signaling may be depicted in exemplary embodiments they are not limited to a certain type of message, and the application is not limited to a certain type of signaling.

Example embodiments provide methods, devices, networks and/or systems, which provide verified and secure machine learning and inference via permissioned blockchains.

A blockchain is a distributed system which includes multiple nodes that communicate with each other. A blockchain operates programs called chaincode (e.g., smart contracts, etc.), holds state and ledger data, and executes transactions. Some transactions are operations invoked on the chaincode. In general, blockchain transactions typically must be "endorsed" by certain blockchain members and only endorsed transactions may be committed to the blockchain and have an effect on the state of the blockchain. Other transactions which are not endorsed are disregarded. There may exist one or more special chaincodes for management functions and parameters, collectively called system chaincodes.

Nodes are the communication entities of the blockchain system. A "node" may perform a logical function in the sense that multiple nodes of different types can run on the same physical server. Nodes are grouped in trust domains and are associated with logical entities that control them in various ways. Nodes may include different types, such as a client or submitting-client node which submits a transaction-invocation to an endorser (e.g., peer), and broadcasts transaction-proposals to an ordering service (e.g., ordering node). Another type of node is a peer node which can receive client submitted transactions, commit the transactions and maintain a state and a copy of the ledger of blockchain transactions. Peers can also have the role of an endorser, although it is not a requirement. An ordering-service-node or orderer is a node running the communication service for all nodes, and which implements a delivery guarantee, such as a broadcast to each of the peer nodes in the system when committing transactions and modifying a world state of the blockchain, which is another name for the initial blockchain transaction which normally includes control and setup information.

A ledger is a sequenced, tamper-resistant record of all state transitions of a blockchain. State transitions may result from chaincode invocations (i.e., transactions) submitted by participating parties (e.g., client nodes, ordering nodes, endorser nodes, peer nodes, etc.). A transaction may result in a set of asset key-value pairs being committed to the ledger as one or more operands, such as creates, updates, deletes, and the like. The ledger includes a blockchain (also referred to as a chain) which is used to store an immutable, sequenced record in blocks. The ledger also includes a state database which maintains a current state of the blockchain. There is typically one ledger per channel. Each peer node maintains a copy of the ledger for each channel of which they are a member.

A chain is a transaction log which is structured as hash-linked blocks, and each block contains a sequence of N transactions where N is equal to or greater than one. The block header includes a hash of the block's transactions, as well as a hash of the prior block's header. In this way, all transactions on the ledger may be sequenced and cryptographically linked together. Accordingly, it is not possible to tamper with the ledger data without breaking the hash links. A hash of a most recently added blockchain block represents every transaction on the chain that has come before it, making it possible to ensure that all peer nodes are in a consistent and trusted state. The chain may be stored on a peer node file system (i.e., local, attached storage, cloud, etc.), efficiently supporting the append-only nature of the blockchain workload.

The current state of the immutable ledger represents the latest values for all keys that are included in the chain transaction log. Because the current state represents the latest key values known to a channel, it is sometimes referred to as a world state. Chaincode invocations execute transactions against the current state data of the ledger. To make these chaincode interactions efficient, the latest values of the keys may be stored in a state database. The state database may be simply an indexed view into the chain's transaction log, it can therefore be regenerated from the chain at any time. The state database may automatically be recovered (or generated if needed) upon peer node startup, and before transactions are accepted.

Supervised Machine Leaning (ML) or Deep Learning (DL) systems require numerous, validated training examples. A single organization may not be able to generate enough examples on its own. By implementing a blockchain for sharing images, inferences, and related data, organizations can benefit from the experience of other similar organizations in a controlled, secure and traceable manner.

In health/safety critical applications, the authenticity, correctness and security of training examples and subsequent inference is critical. In medical diagnosis, for example, doctors must sign-off on the veracity of training examples while preserving patient privacy.

In accordance with example embodiments, a permissioned blockchain network, such as of the type described in more detail below with reference to FIG. 3, may be formed to provide a consortium of organizations who pledge resources to the ML/DL application in exchange for the benefits of sharing training examples and consensus of inference. Pledged resources may include, without limitation, computational resources for executing the blockchain, computational resources for performing machine learning and storage of examples, data resources including training examples, and human resources for provided analysis and verification of examples.

Figure 1:
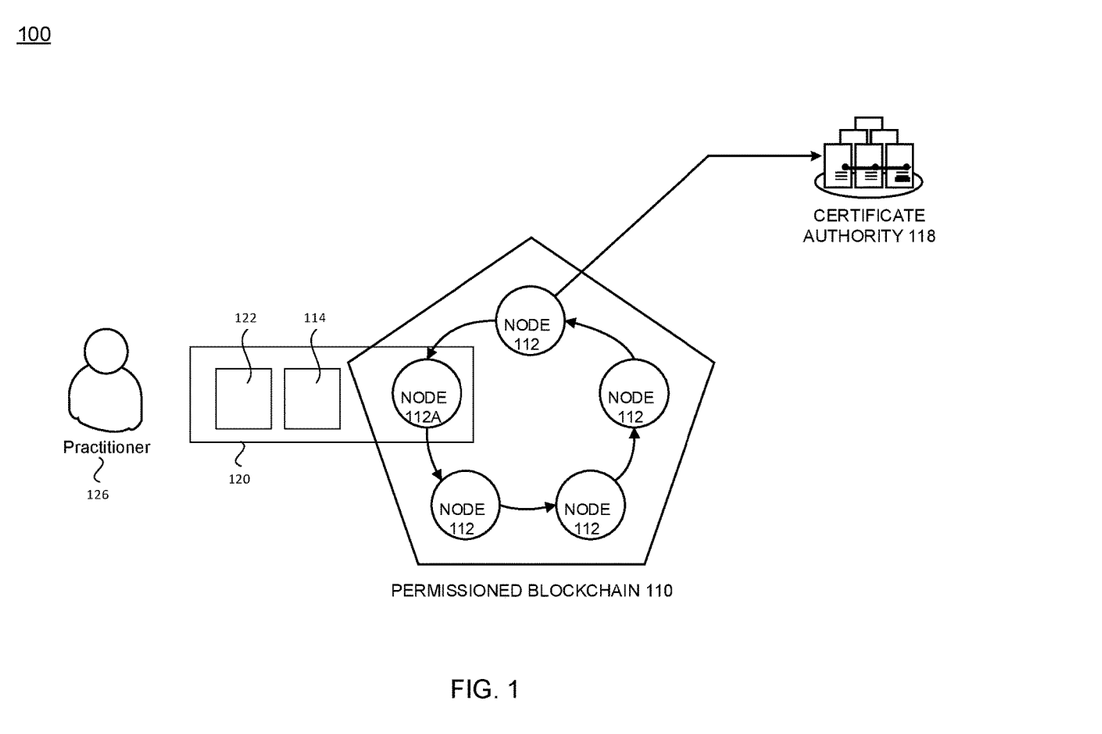
FIG. 1 illustrates a network diagram of a permissioned blockchain, according to example embodiments.

An example of a permissioned blockchain network 100 is depicted generally in FIG. 1. The permissioned blockchain network 110 includes a plurality of endorsing peer nodes 112. The endorsing peers 112 may each be configured to provide automated analysis of the sample data to generate inferences about that data. An organization 120 may operate a client node 114 that is able to contribute sample data and examples for analysis as well as an endorsing peer 112A that can process sample data to generate diagnostic inferences. The organization 120 may store a library 122 of validated examples that can be used by the organization's automated analysis system (e.g. endorsing peer 112A). In specific embodiments, the organization may be a medical diagnostic organization or similar medical practice, though other types of organizations will be apparent to the person skilled in the art. The library 122 may store examples that are validated by the blockchain network 110 as well as offchain examples that have been validated by other means, e.g. privately within the organization.

Membership services and digital certificates may be used via a certificate authority 118 to guarantee that only qualified entities can submit labelled examples and inference requests to the blockchain.

The endorsing peers 112 are programmed so that when a practitioner 126 at an organization 120 submits sample data through the client node 114 to the endorsing peers 112, the endorsing peers undertake automated analysis using machine learning/deep learning algorithms of the sample data to determine an inference for the sample. If consensus of inference is reached across the endorsing nodes during the endorsement phase, then the example may be logged in the blockchain as a validated example. Policies may be used to determine to what degree all endorsing nodes must agree in order for consensus to be reached.

The specific machine learning algorithms are not considered pertinent to the application and different nodes may execute different algorithms to achieve their respective inference on a submitted sample. By having disparate systems achieve consensus of inference, a greater, more reliable outcome is achieved.

The labelled training example, with its consensus of inference, becomes searchable on the blockchain ledger as a validated training example.

Even submitted examples that do not reach consensus can be committed to the blockchain and provide can provide useful training examples to facilitate improvements to the automated analysis system.

Further operational characteristics of a permissioned blockchain network suitable for use in the automated analysis network of FIG. 1 will be described in greater detail below.

Figure 2A:
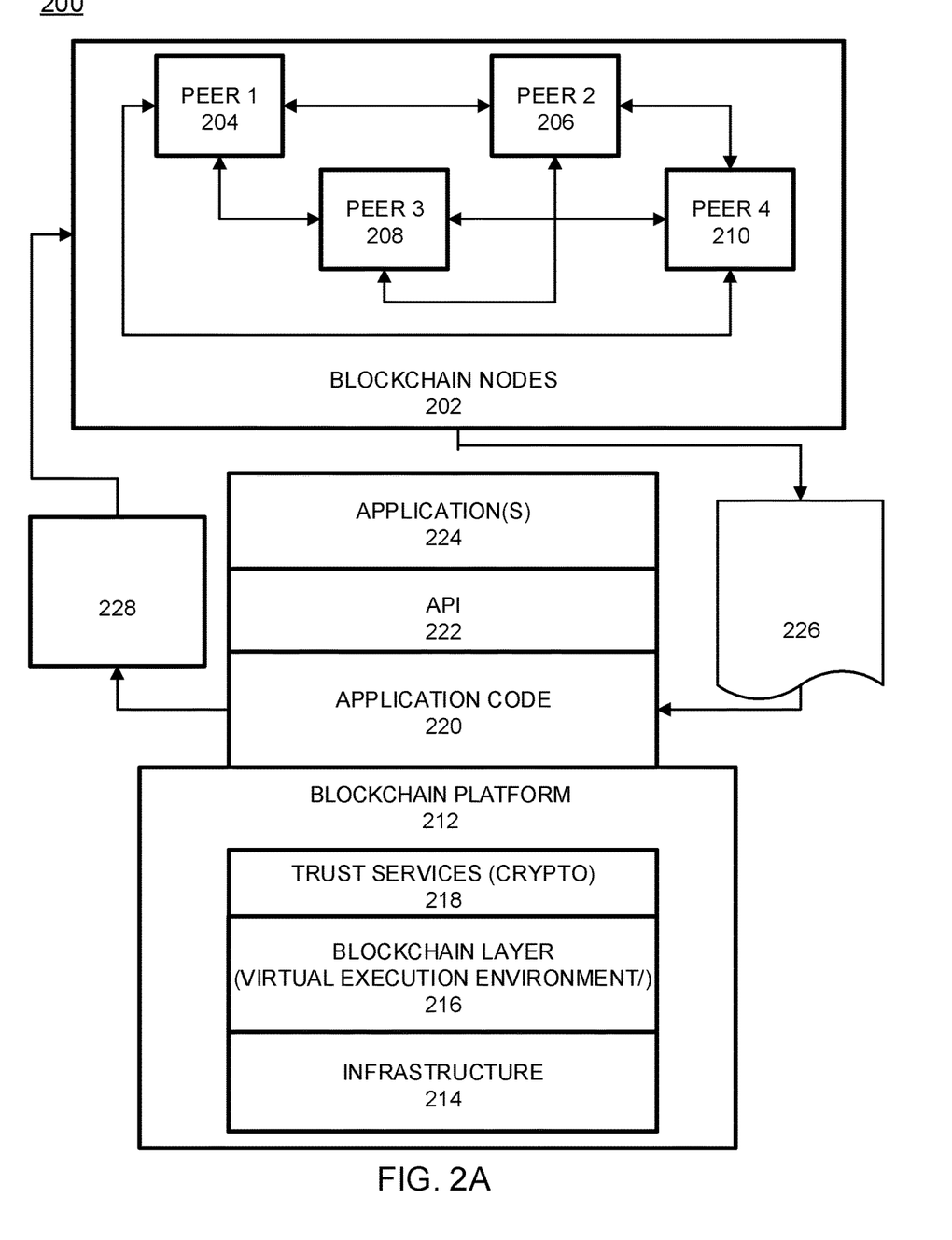
FIG. 2A illustrates an example peer node blockchain architecture configuration for an asset sharing scenario, according to example embodiments.

FIG. 2A illustrates a blockchain architecture configuration 200, according to example embodiments. Referring to FIG. 2A, the blockchain architecture 200 may include certain blockchain elements, for example, a group of blockchain nodes 202. The blockchain nodes 202 may include one or more nodes 204-210. (4 nodes are depicted by example only). These nodes participate in a number of activities, such as blockchain transaction addition and validation process (consensus). One or more of the blockchain nodes 204-210 may endorse transactions and may provide an ordering service for all blockchain nodes in the architecture 200. A blockchain node may initiate a blockchain authentication and seek to write to a blockchain immutable ledger stored in blockchain layer 216, a copy of which may also be stored on the underpinning physical infrastructure 214. The blockchain configuration may include one or more applications 224 which are linked to application programming interfaces (APIs) 222 to access and execute stored program/application code 220 (e.g., chaincode, smart contracts, etc.) which can be created according to a customized configuration sought by participants and can maintain their own state, control their own assets, and receive external information. This can be deployed as a transaction and installed, via appending to the distributed ledger, on all blockchain nodes 204-210.

The blockchain base or platform 212 may include various layers of blockchain data, services (e.g., cryptographic trust services, virtual execution environment, etc.), and underpinning physical computer infrastructure that may be used to receive and store new transactions and provide access to auditors which are seeking to access data entries. The blockchain layer 216 may expose an interface that provides access to the virtual execution environment necessary to process the program code and engage the physical infrastructure 214. Cryptographic trust services 218 may be used to verify transactions such as asset exchange transactions and keep information private.

The blockchain architecture configuration of FIG. 2A may process and execute program/application code 220 via one or more interfaces exposed, and services provided, by blockchain platform 212. The code 220 may control blockchain assets. For example, the code 220 can store and transfer data, and may be executed by nodes 204-210 in the form of a smart contract and associated chaincode with conditions or other code elements subject to its execution. As a non-limiting example, smart contracts may be created to execute reminders, updates, and/or other notifications subject to the changes, updates, etc. The smart contracts can themselves be used to identify rules associated with authorization and access requirements and usage of the ledger. For example, sample data 226 may be processed by one or more processing entities (e.g., virtual machines) included in the blockchain layer 216. The automated analysis and inference result 228 may include an inference drawn on the sample data through machine learning/deep learning algorithms of a node. The physical infrastructure 214 may be utilized to retrieve any of the data or information described herein.

Within chaincode, a smart contract may be created via a high-level application and programming language, and then written to a block in the blockchain. The smart contract may include executable code which is registered, stored, and/or replicated with a blockchain (e.g., distributed network of blockchain peers). A transaction is an execution of the smart contract code which can be performed in response to conditions associated with the smart contract being satisfied. The executing of the smart contract may trigger a trusted modification(s) to a state of a digital blockchain ledger. The modification(s) to the blockchain ledger caused by the smart contract execution may be automatically replicated throughout the distributed network of blockchain peers through one or more consensus protocols.

The smart contract may write data to the blockchain in the format of key-value pairs. Furthermore, the smart contract code can read the values stored in a blockchain and use them in application operations. The smart contract code can write the output of various logic operations into the blockchain. The code may be used to create a temporary data structure in a virtual machine or other computing platform. Data written to the blockchain can be public and/or can be encrypted and maintained as private. The temporary data that is used/generated by the smart contract is held in memory by the supplied execution environment, then deleted once the data needed for the blockchain is identified.

A chaincode may include the code interpretation of a smart contract, with additional features. As described herein, the chaincode may be program code deployed on a computing network, where it is executed and validated by chain validators together during a consensus process. The chaincode receives a hash and retrieves from the blockchain a hash associated with the data template created by use of a previously stored feature extractor. If the hashes of the hash identifier and the hash created from the stored identifier template data match, then the chaincode sends an authorization key to the requested service. The chaincode may write to the blockchain data associated with the cryptographic details. In FIG. 2A, the client submits chaincode including sample data for automated analysis to be performed by the endorsing peers. One function may be to undertake machine learning processes on the submitted sample data to create an inference about the sample data 228, which may be provided to one or more of the nodes 204-210.

Figure 2B:
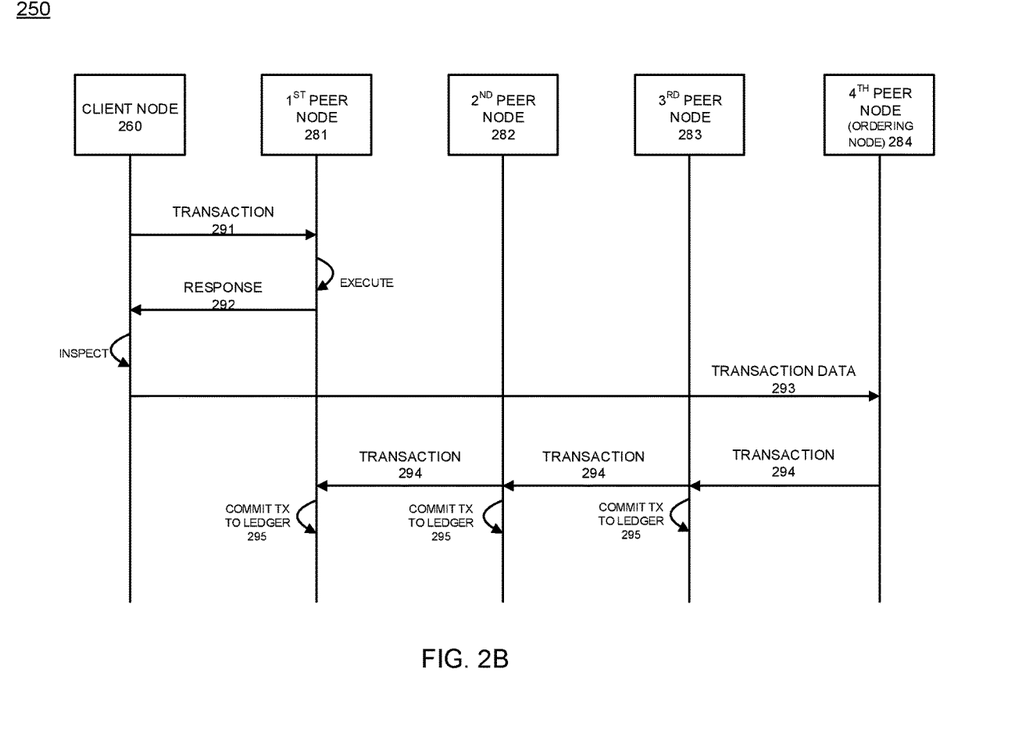
FIG. 2B illustrates an example peer node blockchain configuration, according to example embodiments.

FIG. 2B illustrates an example of a transactional flow 250 between nodes of the blockchain in accordance with an example embodiment. Referring to FIG. 2B, the transaction flow may include a transaction proposal 291 sent by an application client node 260 to an endorsing peer node 281. The endorsing peer 281 may verify the client signature and execute a chaincode function to initiate the transaction. The output may include the chaincode results, a set of key/value versions that were read in the chaincode (read set), and the set of keys/values that were written in chaincode (write set). The proposal response 292 is sent back to the client 260 along with an endorsement signature, if approved. The client 260 assembles the endorsements into a transaction payload 293 and broadcasts it to an ordering service node 284. The ordering service node 284 then delivers ordered transactions as blocks to all peers 281-283 on a channel. Before committal to the blockchain, each peer 281-283 may validate the transaction. For example, the peers may check the endorsement policy to ensure that the correct allotment of the specified peers have signed the results and authenticated the signatures against the transaction payload 293.

Referring again to FIG. 2B, the client node 260 initiates the transaction 291 by constructing and sending a request to the peer node 281, which is an endorser. The client 260 may include an application leveraging a supported software development kit (SDK), such as NODE, JAVA, PYTHON, and the like, which utilizes an available API to generate a transaction proposal. The proposal is a request to invoke a chaincode function so that data can be read and/or written to the ledger (i.e., write new key value pairs for the assets). The SDK may serve as a shim to package the transaction proposal into a properly architected format (e.g., protocol buffer over a remote procedure call (RPC)) and take the client's cryptographic credentials to produce a unique signature for the transaction proposal.

In response, the endorsing peer node 281 may verify (a) that the transaction proposal is well formed, (b) the transaction has not been submitted already in the past (replay-attack protection), (c) the signature is valid, and (d) that the submitter (client 260, in the example) is properly authorized to perform the proposed operation on that channel. The endorsing peer node 281 may take the transaction proposal inputs as arguments to the invoked chaincode function. The chaincode is then executed against a current state database to produce transaction results including a response value, read set, and write set. However, no updates are made to the ledger at this point. In 292, the set of values, along with the endorsing peer node's 281 signature is passed back as a proposal response 292 to the SDK of the client 260 which parses the payload for the application to consume.

In response, the application of the client 260 inspects/verifies the endorsing peers signatures and compares the proposal responses to determine if the proposal response is the same. If the chaincode only queried the ledger, the application would inspect the query response and would typically not submit the transaction to the ordering node service 284. If the client application intends to submit the transaction to the ordering node service 284 to update the ledger, the application determines if the specified endorsement policy has been fulfilled before submitting (i.e., did all peer nodes necessary for the transaction endorse the transaction). Here, the client may include only one of multiple parties to the transaction. In this case, each client may have their own endorsing node, and each endorsing node will need to endorse the transaction. The architecture is such that even if an application selects not to inspect responses or otherwise forwards an unendorsed transaction, the endorsement policy will still be enforced by peers and upheld at the commit validation phase.

After successful inspection, in step 293 the client 260 assembles endorsements into a transaction and broadcasts the transaction proposal and response within a transaction message to the ordering node 284. The transaction may contain the read/write sets, the endorsing peers signatures and a channel ID. The ordering node 284 does not need to inspect the entire content of a transaction in order to perform its operation, instead the ordering node 284 may simply receive transactions from all channels in the network, order them chronologically by channel, and create blocks of transactions per channel.

The blocks of the transaction are delivered from the ordering node 284 to all peer nodes 281-283 on the channel. The transactions 294 within the block are validated to ensure any endorsement policy is fulfilled and to ensure that there have been no changes to ledger state for read set variables since the read set was generated by the transaction execution. Transactions in the block are tagged as being valid or invalid. Furthermore, in step 295 each peer node 281-283 appends the block to the channel's chain, and for each valid transaction the write sets are committed to current state database. An event is emitted, to notify the client application that the transaction (invocation) has been immutably appended to the chain, as well as to notify whether the transaction was validated or invalidated.

Figure 3:
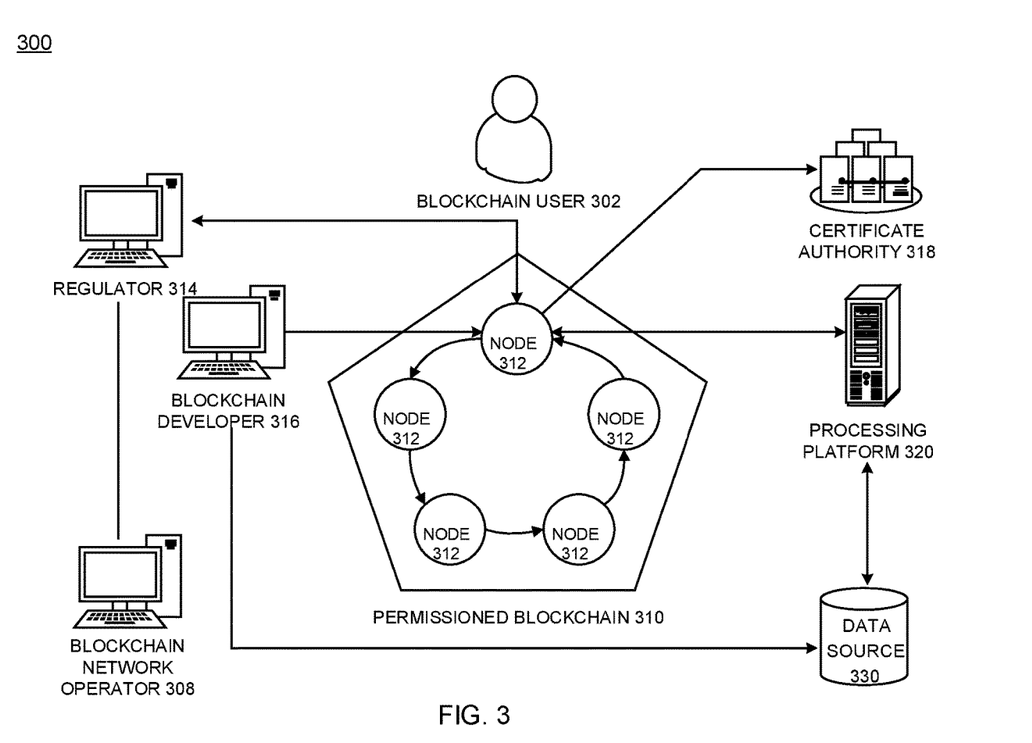
FIG. 3 is a diagram illustrating a permissioned blockchain network, according to example embodiments.

FIG. 3 illustrates an example of a permissioned blockchain network 300, which features a distributed, decentralized peer-to-peer architecture, and a certificate authority 318 managing user roles and permissions. In this example, the blockchain user 302 may submit a transaction to the permissioned blockchain network 310. In this example, the transaction can be a deploy, invoke or query, and may be issued through a client-side application leveraging an SDK, directly through a REST API, or the like. Trusted business networks may provide access to regulator systems 314, such as auditors (the Securities and Exchange Commission in a U.S. equities market, for example). Meanwhile, a blockchain network operator system of nodes 308 manage member permissions, such as enrolling the regulator system 310 as an "auditor" and the blockchain user 302 as a "client." An auditor could be restricted only to querying the ledger whereas a client could be authorized to deploy, invoke, and query certain types of chaincode.

A blockchain developer system 316 writes chaincode and client-side applications. The blockchain developer system 316 can deploy chaincode directly to the network through a REST interface. To include credentials from a traditional data source 330 in chaincode, the developer system 316 could use an out-of-band connection to access the data. In this example, the blockchain user 302 connects to the network through a peer node 312. Before proceeding with any transactions, the peer node 312 retrieves the user's enrollment and transaction certificates from the certificate authority 318. In some cases, blockchain users must possess these digital certificates in order to transact on the permissioned blockchain network 310. Meanwhile, a user attempting to drive chaincode may be required to verify their credentials on the traditional data source 330. To confirm the user's authorization, chaincode can use an out-of-band connection to this data through a traditional processing platform 320.

Figure 4:
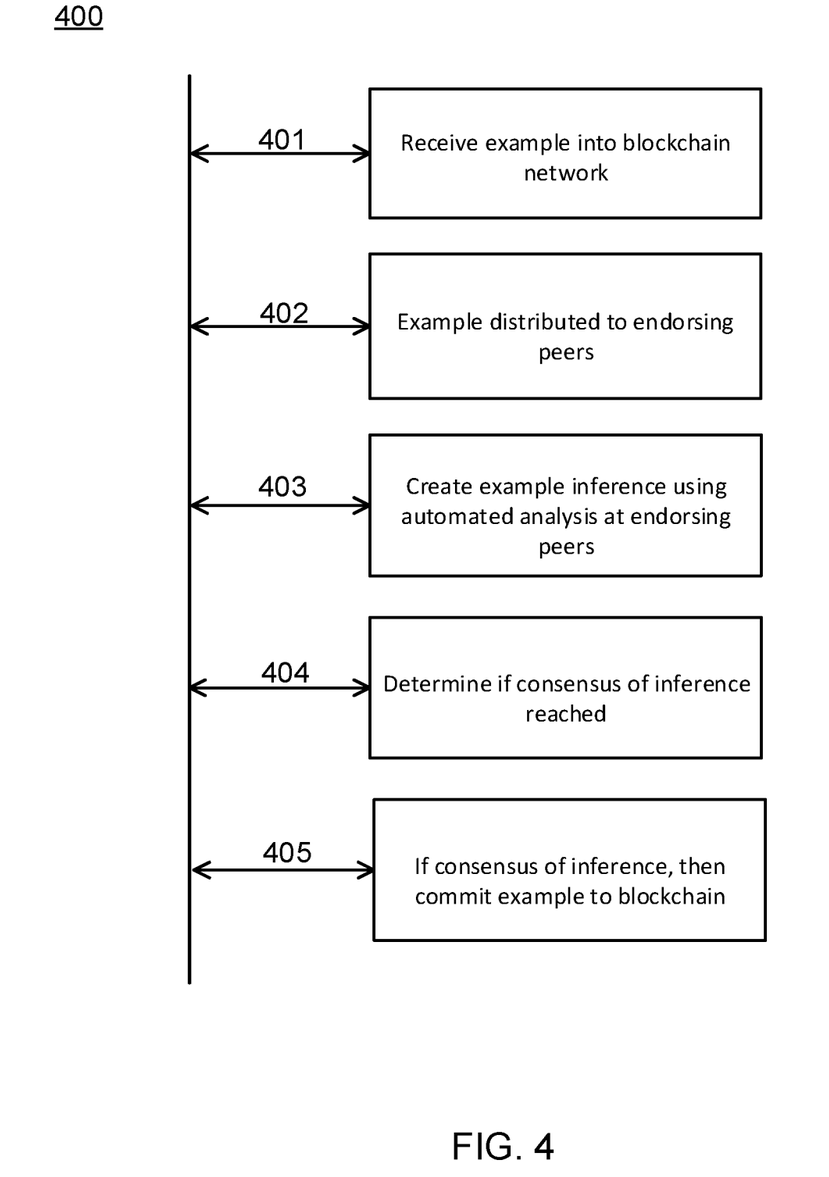
FIG. 4 illustrates a flow diagram for an automated analysis blockchain network according to example embodiments.

FIG. 4 shows a process 400 for automated analysis of sample data on a permissioned blockchain. At step 401, a user, submits an example to the blockchain network which is received into the blockchain network and distributed to a plurality of endorsing peers (402) in accordance with a policy. The plurality of endorsing peers each apply automated analysis to the example (403) to create an inference. At step 404, consensus services determine if a consensus of inference has been reached. Consensus of inference may be determined with reference to a policy stored within each endorsing peer or within an organization network. When consensus has been determined to have been achieved, the submitted example may be validated and recorded on the blockchain 405. In one embodiment, only the validation and endorsement is stored on the blockchain with the specific example data being stored off-chain in a manner that allows all parties to have access to the data. In an alternative example, the example data may itself be incorporated into the blockchain.

Once a consensus of analysis is achieved, the example can be added to a library of examples (on or off-chain) that is used by a machine learning system in an automated analysis of subsequent examples.

In order for training to be effective, it is necessary to have training examples with both positive (e.g. this IS a cat) and negative labels (e.g. this IS NOT a cat). Therefore, consensus may result in a positive label or a negative label being applied to the example. In addition, examples that don't reach consensus may be tagged as "indeterminate", "unresolved" or some similar label and logged into the blockchain. For examples that are unresolved, differences in inference by the different endorsing peers may be recorded and logged in the blockchain, thereby providing useful additional data that may assist in future determinations on similar examples.

In one embodiment, the user may submit the example via a client node 114 which distributes the example to all endorsing peers 112 concurrently. The client node may invoke chaincode to form the example data, e.g. including a medical image for diagnosis, into a transaction proposal. The endorsing peers use chaincode and their own automated analysis systems to generate an inference for the transaction which is returned, signed by the endorsing peer, to the submitting client node 114. The client node collects the inferences and performs consensus checking, with reference to a consensus policy. If consensus is reached, the submitting client node may submit the endorsed transaction to an ordering node which may then commit the example to the blockchain and transmit a transaction block to the endorsing peers. The endorsing peers can update the ledgers with the block containing the new training example.

Organizations maintain the state of the blockchain ledger within their own organization, e.g. via their own endorsing peer node 112A. The ledger becomes a searchable library of training examples that can be used by the organization's own automated analysis systems, potentially together with other offchain examples that the organization may have access to.

Consensus services operated by the peer nodes guarantee that multiple (disparate) systems agree to the inference. Or at least, differences are recorded. Each inference is signed/validated by each endorsing peer that performs the automated analysis. All data and inference that is recorded into the blockchain is immutable and its provenance is tracked, thereby providing an inference record that can be scrutinized by any relevant party to enable their particular machine learning system to be improved.

Sharing of examples and, importantly, sharing of inference, can benefit all parties in the improvement of their machine learning systems.

Figure 5:
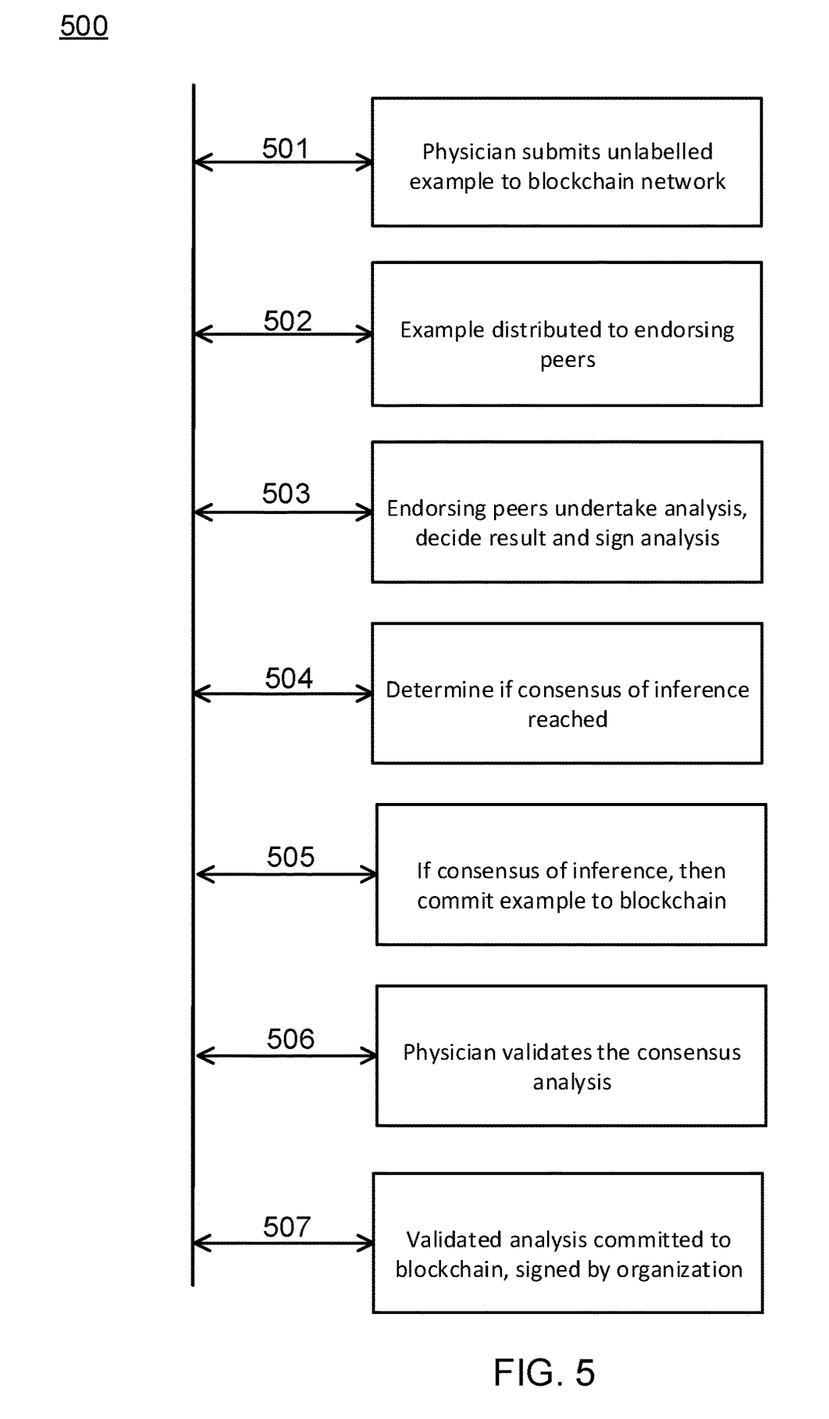
FIG. 5 illustrates a flow diagram of an example method of analyzing a medical image in a blockchain network, according to example embodiments.

FIG. 5 shows a flowchart 500 for a particular example for a medical diagnosis system. In this example, a physician submits an unlabeled medical image to the blockchain network 501. The image is distributed to multiple (disparate) automated analysis systems during the endorsement phase (502). Each analysis system undertakes an analysis, decides a result (inference) and signs its analysis (503). If automated analysis agrees (consensus) across the required number of systems 504, as determined by a consensus or endorsement policy, then the image and analysis is logged in the blockchain as a valid training example 505. In order to reduce data size of the blockchain and/or to protect patient privacy, a hash of the image may be logged in place of the actual image.

Examples that don't reach consensus may be particularly valuable as indeterminate or unresolved training examples.

At a future time, the (or another) physician validates the analysis 506. If the analysis is correct, another blockchain transaction (signed by the physician or her organization) marks the automated analysis as valid and suitable for use as a training example 507 for the machine learning/deep learning model.

Each entity in the consortium could have its own proprietary system. Thus, if consensus is reached via disparate systems, then the strength or relevance of the example as a training example for the machine learning is enhanced, which is of benefit to all systems in the blockchain network.

The blockchain network enhances automated diagnosis by providing for traceability of the exact software (state) that was used to perform the diagnosis. Consensus of inference (diagnosis, classification) from multiple (disparate) intelligent agents is also provided. Furthermore, the blockchain network allows consortium members to share the expense and benefits of expert human classification of training examples.

The permissioned blockchain network could be operated in various ways. For example, a consortium of entities could set up a service amongst themselves, and charge other entities for use of the service, i.e. to access a library of validated examples. Smart contracts could enforce requirements that participants must provide a certain number of certified labelled examples in exchange for a certain number of inference requests. An entity might process most of its data through a private system, but still join the consortium for access to a variety of different training examples. An ML/DL company selling inference software might elect to distribute the software as a blockchain network.

In one specific example, Hospital A might submit an MRI and ECG of a patient to the permissioned blockchain, which they cannot diagnose with their ML (machine learning) system. By consensus, Hospitals B, C, and D may conclude that the patient has condition X, by analyzing the MRI of the patient. By logging the results in the blockchain, now each Hospital system has a set of ECG data which is associated to condition X which was not previously available. Hence the "labeled" ECG data can now be used to train or improve the ML systems for the ECG data. This would not be available without the consensus, and Hospitals B, C and D would not be able to do this because they did not have the patient data to connect the condition X to the ECG data. Thus, by sharing of examples through a permissioned blockchain, with consensus of diagnosis, improved machine learning and patient outcomes can be achieved.

The present embodiments utilize many of the advantageous aspects of a blockchain network for enhancing machine learning outcomes, particularly in an automated diagnostic and analysis field. The accountability and endorsement is crucial for this ensuring accurate analysis and that training examples are correctly labelled (e.g. positive, negative, etc.). The security is needed for ML applications in the medical field.

Figure 6A:
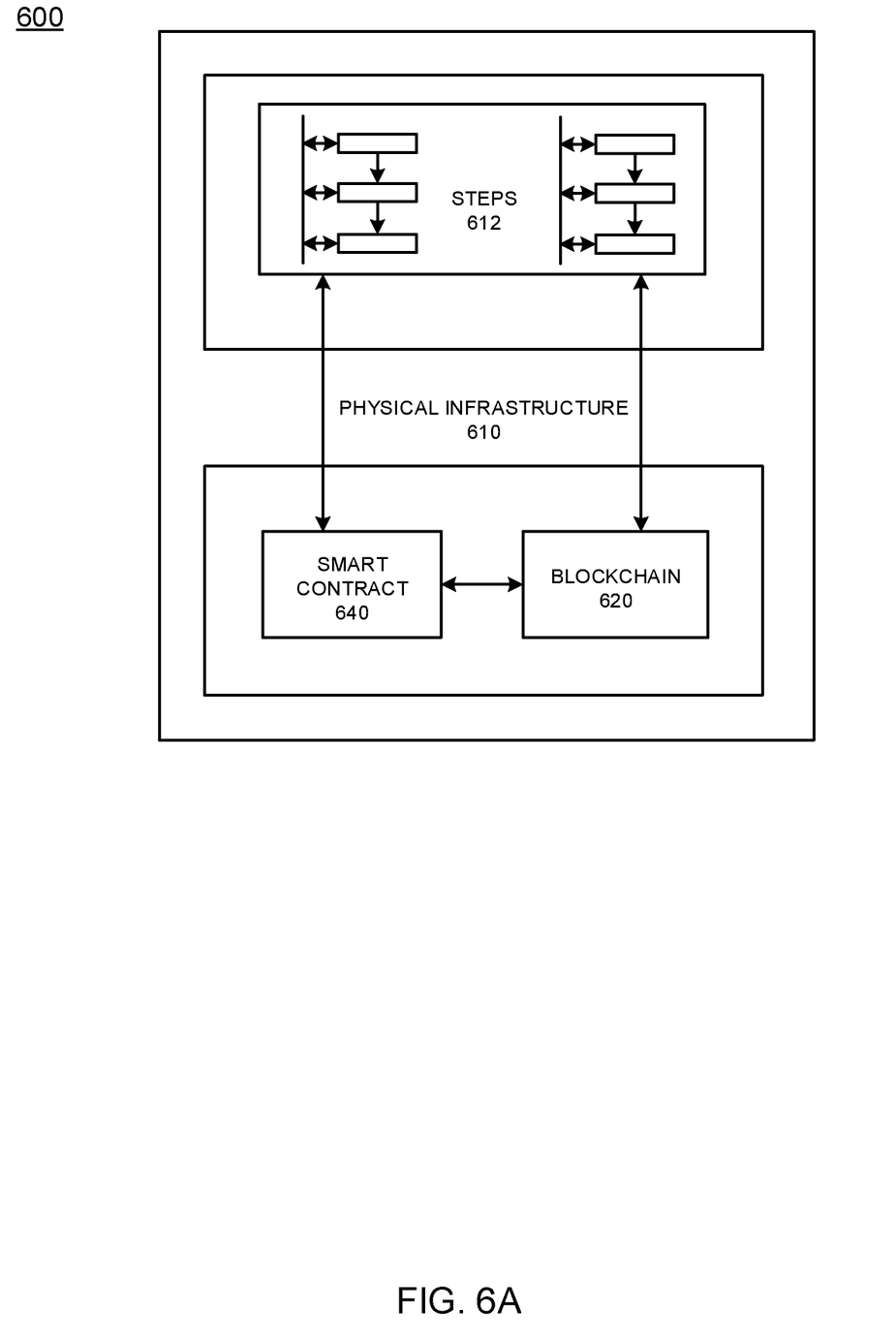
FIG. 6A illustrates an example physical infrastructure configured to perform various operations on the blockchain in accordance with one or more operations described herein, according to example embodiments.

FIG. 6A illustrates an example physical infrastructure configured to perform various operations on the blockchain in accordance with one or more of the example methods of operation according to example embodiments. Referring to FIG. 6A, the example configuration 600 includes a physical infrastructure 610 with a blockchain 620 and a smart contract 640, which may execute any of the operational steps 612 included in any of the example embodiments. The steps/operations 612 may include one or more of the steps described or depicted in one or more flow diagrams and/or logic diagrams. The steps may represent output or written information that is written or read from one or more smart contracts 640 and/or blockchains 620 that reside on the physical infrastructure 610 of a computer system configuration. The data can be output from an executed smart contract 640 and/or blockchain 620. The physical infrastructure 610 may include one or more computers, servers, processors, memories, and/or wireless communication devices.

Figure 6B:
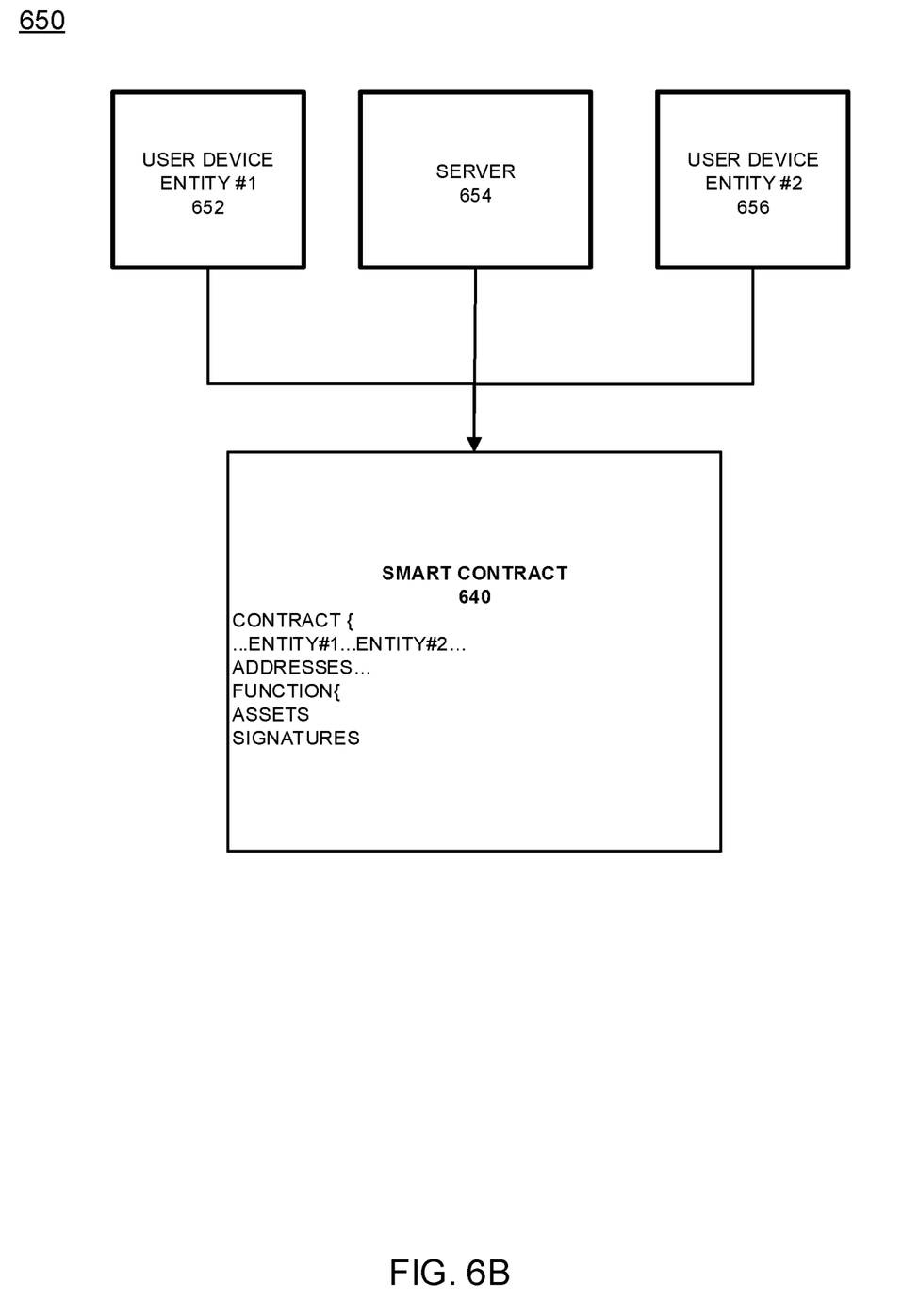
FIG. 6B illustrates an example smart contract configuration among contracting parties and a mediating server configured to enforce smart contract terms on a blockchain, according to example embodiments.

FIG. 6B illustrates an example smart contract configuration among contracting parties and a mediating server configured to enforce the smart contract terms on the blockchain according to example embodiments. Referring to FIG. 6B, the configuration 650 may represent a communication session, an asset transfer session or a process or procedure that is driven by a smart contract 640 which explicitly identifies one or more user devices 652 and/or 656. The execution, operations and results of the smart contract execution may be managed by a server 654. Content of the smart contract 640 may require digital signatures by one or more of the entities 652 and 656 which are parties to the smart contract transaction. The results of the smart contract execution may be written to a blockchain as a blockchain transaction.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 7 illustrates an example computer system architecture 700, which may represent or be integrated in any of the above-described components, etc.

Figure 7:
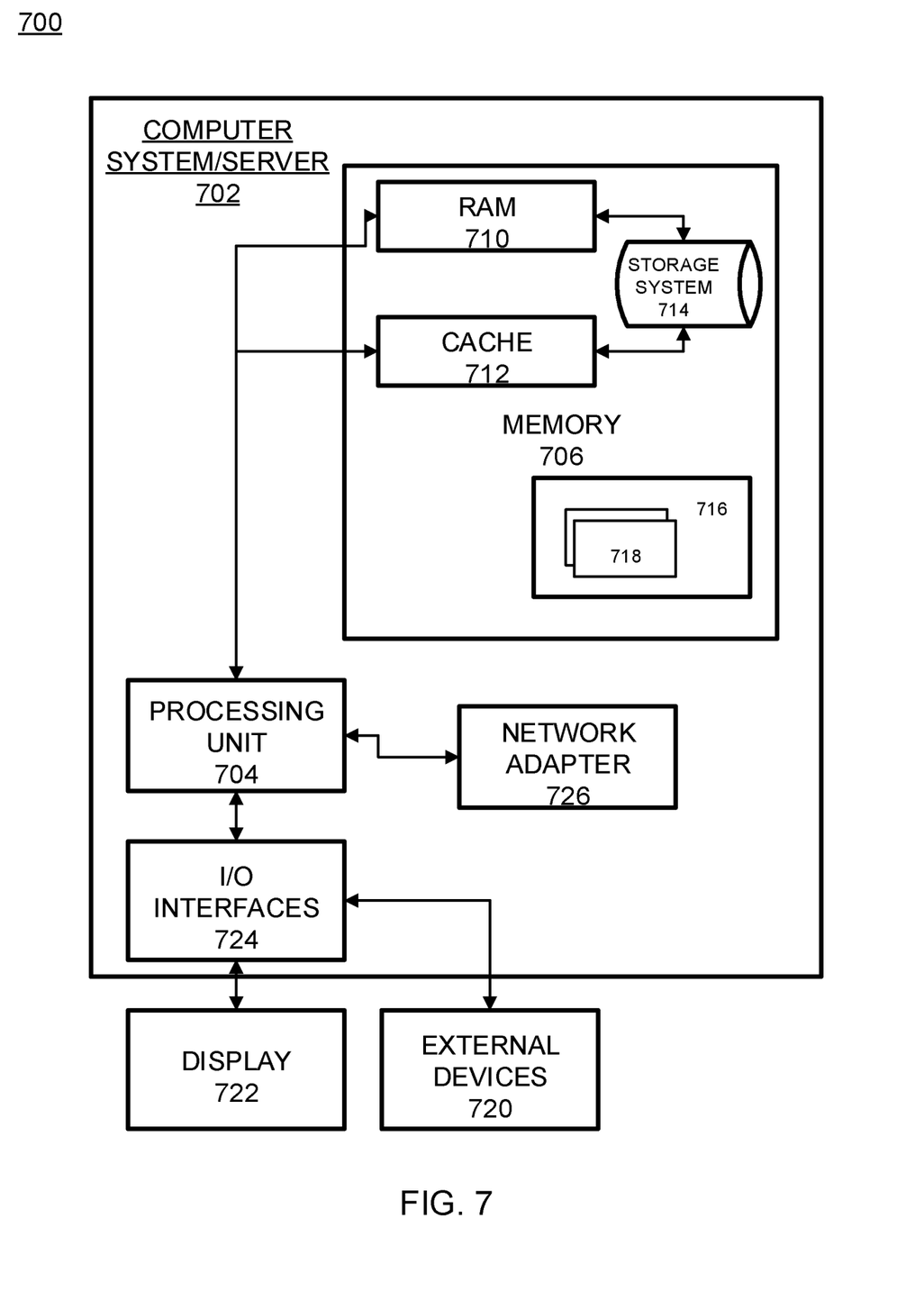
FIG. 7 illustrates an example computer system configured to support one or more of the example embodiments.

FIG. 7 is not intended to suggest any limitation as to the scope of use or functionality of embodiments of the application described herein. Regardless, the computing node 700 is capable of being implemented and/or performing any of the functionality set forth hereinabove.

In computing node 700 there is a computer system/server 702, which is operational with numerous other general purpose or special purpose computing system environments or configurations. Examples of well-known computing systems, environments, and/or configurations that may be suitable for use with computer system/server 702 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 702 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 702 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 702 in cloud computing node 700 is shown in the form of a general-purpose computing device. The components of computer system/server 702 may include, but are not limited to, one or more processors or processing units 704, a system memory 706, and a bus that couples various system components including system memory 706 to processor 704.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 702 typically includes a variety of computer system readable media. Such media may be any available media that is accessible by computer system/server 702, and it includes both volatile and non-volatile media, removable and non-removable media. System memory 706, in one embodiment, implements the flow diagrams of the other figures. The system memory 706 can include computer system readable media in the form of volatile memory, such as random-access memory (RAM) 710 and/or cache memory 712. Computer system/server 702 may further include other removable/non-removable, volatile/non-volatile computer system storage media. By way of example only, storage system 714 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 706 may include at least one program product having a set (e.g., at least one) of program modules that are configured to carry out the functions of various embodiments of the application.

Program/utility 716, having a set (at least one) of program modules 718, may be stored in memory 706 by way of example, and not limitation, as well as an operating system, one or more application programs, other program modules, and program data. Each of the operating system, one or more application programs, other program modules, and program data or some combination thereof, may include an implementation of a networking environment. Program modules 718 generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Computer system/server 702 may also communicate with one or more external devices 720 such as a keyboard, a pointing device, a display 722, etc.; one or more devices that enable a user to interact with computer system/server 702; and/or any devices (e.g., network card, modem, etc.) that enable computer system/server 702 to communicate with one or more other computing devices. Such communication can occur via I/O interfaces 724. Still yet, computer system/server 702 can communicate with one or more networks such as a local area network (LAN), a general wide area network (WAN), and/or a public network (e.g., the Internet) via network adapter 726. As depicted, network adapter 726 communicates with the other components of computer system/server 702 via a bus. It should be understood that although not shown, other hardware and/or software components could be used in conjunction with computer system/server 702. Examples, include, but are not limited to: microcode, device drivers, redundant processing units, external disk drive arrays, RAID systems, tape drives, and data archival storage systems, etc.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method, comprising:
receiving data for a machine learning model via a blockchain network, wherein the blockchain network enforce requirements that participants must provide a number of certified labelled examples in exchange for the number of inference requests;
distributing the data to a plurality of endorsing peers of the blockchain network wherein the endorsing peer verify client signature;
executing, by the plurality of endorsing peers, the machine learning model on the data to generate a plurality of inferences from the data via the plurality of endorsing peers of the blockchain network, respectively;
determining, by automated analysis, that a consensus does not exist amongst the plurality of inferences generated via the plurality of endorsing peers based on differences in the plurality of inferences generated by the plurality of endorsing peers and a policy that specifies a degree that the plurality of endorsing peers must agree to achieve the consensus;
labeling the data as unresolved when consensus does not reach;
collecting the inferences and committing transaction on the labeled data based on the different inferences of the plurality of endorsing peers to a blockchain ledger of the blockchain network; and
updating the ledger with new training example by the endorsing peers.

2. The method of claim 1 wherein the determining comprises referencing an endorsement policy that specifies how the consensus is determined.

3. The method of claim 1 wherein one or more of the endorsing peers comprises a machine learning system that is programmed to execute the machine learning model with reference to a plurality of validated training data sets stored within a library of validated examples on the blockchain ledger.

4. The method of claim 3 wherein the plurality of endorsing peers operate disparate machine learning systems.

5. The method of claim 1 wherein the data is an unlabeled medical image.

6. The method of claim 1 further comprising storing an indeterminate training example on the blockchain ledger in response to determining that the consensus does not exist.

7. A system comprising:
a blockchain network comprising a plurality of endorsing peers, wherein the blockchain network comprises one or more processing devices configured to:
receive data for a machine learning model and distribute the data to the plurality of the endorsing peers, wherein the blockchain network enforce requirements that participants must provide a number of certified labelled examples in exchange for the number of inference requests, wherein the endorsing peer verify client signature;
execute, by the plurality of endorsing peers, the machine learning model on the data to generate a plurality of inferences from the data via the plurality of endorsing peers of the blockchain network, respectively;
determine, by automated analysis, that a consensus does not exist amongst the plurality of inferences generated via the plurality of endorsing peers based on differences in the plurality of inferences generated by the plurality of endorsing peers and a policy that specifies a degree that the plurality of endorsing peers must agree to achieve the consensus;
label the data as unresolved when consensus does not reach;
collect the inferences and commit transaction on the labeled data based on the different inferences of the plurality of endorsing peers to a blockchain ledger of the blockchain network; and
update the ledger with new training example by the endorsing peers.

8. The system of claim 7 wherein the blockchain network stores one or more endorsement policies that specify how the consensus is determined.

9. The system of claim 7 wherein one or more of the endorsing peers comprises a machine learning system that is programmed to execute the machine learning model with reference to a plurality of validated examples stored within a library of validated examples on the blockchain ledger.

10. The system of claim 9 wherein the plurality of endorsing peers operate disparate machine learning systems.

11. The system of claim 7 wherein the data is an unlabeled medical image.

12. The system of claim 7 wherein the blockchain network is configured to store an indeterminate training example on the blockchain ledger in response to determining that the consensus does not exist.

13. The system of claim 7 wherein the blockchain network is a permissioned blockchain network.

14. A non-transitory computer readable medium comprising instructions, that when read by a processor, cause the processor to perform:
receiving data for a machine learning model via a blockchain network wherein the blockchain network enforce requirements that participants must provide a number of certified labelled examples in exchange for the number of inference requests;
distributing the data to a plurality of endorsing peers of the blockchain network wherein the endorsing peer verify client signature;
executing, by the plurality of endorsing peers, the machine learning model on the data to generate a plurality of inferences from the data via the plurality of endorsing peers of the blockchain network, respectively;
determining by automated analysis, that a consensus does not exist amongst the plurality of interferences generated via the plurality of endorsing peers based on differences in the plurality of inferences generated by the plurality of endorsing peers and a policy that specifies a degree that the plurality of endorsing peers must agree to achieve the consensus;

labeling the data as unresolved when consensus does not reach;

collecting the inferences and committing transaction on the labeled data based on the different inferences of the plurality of endorsing peers to a blockchain ledger of the blockchain network; and updating the ledger new training example by the endorsing peers.

15. The non-transitory computer readable medium of claim 14 wherein the determining comprises referencing an endorsement policy that specifies how the consensus is determined.

16. The non-transitory computer readable medium of claim 14 wherein one or more of the endorsing peers comprises a machine learning system comprising instructions for executing the machine learning model with reference to a plurality of validated examples stored within a library of validated examples on the blockchain ledger.

17. The non-transitory computer readable medium of claim 14 comprising instructions for storing an indeterminate training example on the blockchain ledger in response to determining that the consensus does not exist.

* * * * *